(12) United States Patent
Grignani et al.

(10) Patent No.: US 8,084,076 B2
(45) Date of Patent: Dec. 27, 2011

(54) PROCESS FOR PRODUCING STENTS AND CORRESPONDING STENTS

(75) Inventors: Andrea Grignani, Chieri (IT); Maria Curcio, Saluggia (IT); Vincenzo Cassolaro, Saluggia (IT)

(73) Assignee: Sorin Biomedica Cardio S.R.L., Saluggia (Vercelli) (IT)

( * ) Notice: Subject to any disclaimer, the term of this patent is extended or adjusted under 35 U.S.C. 154(b) by 863 days.

(21) Appl. No.: 12/027,347

(22) Filed: Feb. 7, 2008

(65) Prior Publication Data

US 2008/0140186 A1 Jun. 12, 2008

Related U.S. Application Data

(63) Continuation of application No. 10/782,412, filed on Feb. 19, 2004, now abandoned.

(30) Foreign Application Priority Data

Feb. 21, 2003 (EP) ..................... 03425106

(51) Int. Cl.
  *B05D 3/10* (2006.01)
  *B05D 1/00* (2006.01)
  *B05D 1/40* (2006.01)
  *A61F 2/06* (2006.01)

(52) U.S. Cl. ....... 427/2.24; 427/2.1; 427/2.25; 427/256; 427/261; 427/271; 427/282; 427/277; 427/278; 427/331; 427/335; 623/1.42; 623/1.44; 623/1.46

(58) Field of Classification Search .............. 427/2.1, 427/2.24, 2.25, 256, 264, 265, 271, 335; 623/1.44, 1.46

See application file for complete search history.

(56) References Cited

U.S. PATENT DOCUMENTS

| 3,727,577 A | * | 4/1973 | McGarr et al. ............ 118/630 |
| 5,084,151 A | | 1/1992 | Vallana et al. |
| 5,133,845 A | | 7/1992 | Vallana et al. |
| 5,370,684 A | | 12/1994 | Vallana et al. |
| 5,387,247 A | | 2/1995 | Vallana et al. |
| 5,423,886 A | | 6/1995 | Arru et al. |
| 5,837,313 A | | 11/1998 | Ding et al. |
| 5,925,402 A | | 7/1999 | Nacker et al. |

(Continued)

FOREIGN PATENT DOCUMENTS

CA 2 435 306 8/2002

(Continued)

OTHER PUBLICATIONS

European Search Report for EP 03425106.6 (3 pages).

(Continued)

*Primary Examiner* — Timothy Meeks
*Assistant Examiner* — Cachet Sellman
(74) *Attorney, Agent, or Firm* — Popovich, Wiles & O'Connell, P.A.

(57) ABSTRACT

A process for depositing an active substance on selected regions of the surface of a stent, comprising: (i) providing the active substance in at least one form selected from the group consisting of a powder and a paste; and (ii) depositing the active substance on the selected regions of the surface of the stent.

Preferably, the active substance comprises or consists essentially of FK506, such as FK506 in the form of a powder with a grain size smaller than 15 micron or a paste with a base of FK506 with a viscosity not lower than 100,000 to 120,000 cps.

42 Claims, 6 Drawing Sheets

U.S. PATENT DOCUMENTS

| | | | |
|---|---|---|---|
| 6,120,536 A | 9/2000 | Ding et al. | |
| 6,120,847 A * | 9/2000 | Yang et al. | 427/335 |
| 6,153,252 A | 11/2000 | Hossainy et al. | |
| 6,156,373 A | 12/2000 | Zhong et al. | |
| 6,254,632 B1 | 7/2001 | Wu et al. | |
| 6,273,908 B1 | 8/2001 | Ndondo-Lay | |
| 6,273,913 B1 | 8/2001 | Wright et al. | |
| 6,325,821 B1 | 12/2001 | Gaschino et al. | |
| 6,358,556 B1 | 3/2002 | Ding et al. | |
| 6,364,856 B1 | 4/2002 | Ding et al. | |
| 6,368,658 B1 | 4/2002 | Schwarz et al. | |
| 6,395,326 B1 * | 5/2002 | Castro et al. | 427/2.24 |
| 6,451,050 B1 | 9/2002 | Rudakov et al. | |
| 6,613,083 B2 | 9/2003 | Alt | |
| 6,620,194 B2 | 9/2003 | Ding et al. | |
| 6,624,138 B1 | 9/2003 | Sung et al. | |
| 6,627,246 B2 | 9/2003 | Mehta et al. | |
| 6,638,302 B1 | 10/2003 | Curcio et al. | |
| 6,652,581 B1 | 11/2003 | Ding | |
| 6,670,398 B2 | 12/2003 | Edwards et al. | |
| 6,676,987 B2 | 1/2004 | Zhong et al. | |
| 6,743,463 B2 | 6/2004 | Weber et al. | |
| 6,743,643 B2 | 6/2004 | Joshi et al. | |
| 6,746,773 B2 | 6/2004 | Llanos et al. | |
| 6,776,796 B2 | 8/2004 | Falotico et al. | |
| 6,787,179 B2 | 9/2004 | Timm et al. | |
| 6,833,004 B2 | 12/2004 | Ishii et al. | |
| 6,852,122 B2 | 2/2005 | Rush | |
| 6,861,088 B2 | 3/2005 | Weber et al. | |
| 6,884,429 B2 | 4/2005 | Koziak et al. | |
| 6,890,463 B2 | 5/2005 | Martakos et al. | |
| 6,890,546 B2 | 5/2005 | Mollison et al. | |
| 6,893,859 B2 | 5/2005 | Ashley et al. | |
| 6,896,965 B1 | 5/2005 | Hossainy | |
| 6,908,622 B2 | 6/2005 | Barry et al. | |
| 2001/0049551 A1 * | 12/2001 | Tseng et al. | 623/1.15 |
| 2003/0028242 A1 | 2/2003 | Vallana et al. | |
| 2003/0134052 A1 | 7/2003 | Dave | |
| 2003/0190547 A1 * | 10/2003 | Kobayashi et al. | 430/125 |
| 2004/0059409 A1 * | 3/2004 | Stenzel | 623/1.15 |
| 2004/0202773 A1 | 10/2004 | Verlee et al. | |

FOREIGN PATENT DOCUMENTS

| | | |
|---|---|---|
| EP | 0 551 182 A1 | 7/1993 |
| EP | 0 747 069 A2 | 12/1996 |
| EP | 0 806 190 A1 | 11/1997 |
| EP | 0 850 604 A2 | 7/1998 |
| EP | 0 875 215 A1 | 11/1998 |
| EP | 0 895 759 A1 | 2/1999 |
| EP | 0 895 760 A1 | 2/1999 |
| EP | 0 950 386 A2 | 10/1999 |
| EP | 0 970 711 A2 | 1/2000 |
| EP | 1 080 738 A1 | 3/2001 |
| EP | 1 088 528 A1 | 4/2001 |
| EP | 1 103 234 A1 | 5/2001 |
| EP | 1 174 098 A2 | 1/2002 |
| EP | 1 181 903 A2 | 2/2002 |
| EP | 1 212 986 A1 | 6/2002 |
| EP | 1 254 673 A1 | 11/2002 |
| EP | 1 254 674 A1 | 11/2002 |
| EP | 1 277 449 A1 | 1/2003 |
| WO | WO 98/08482 A2 | 3/1998 |
| WO | WO 01/82833 A2 | 11/2001 |
| WO | WO 01/87368 A1 | 11/2001 |
| WO | WO 02/26280 A1 | 4/2002 |
| WO | WO 02/26281 A1 | 4/2002 |
| WO | WO 02/47739 A2 | 6/2002 |
| WO | WO 02/056790 A2 | 7/2002 |
| WO | WO 02/065947 A2 | 8/2002 |
| WO | WO 02/093988 A1 | 11/2002 |

OTHER PUBLICATIONS

Jun. 28, 2007 Communication Pursuant to Article 96(2) EPC for counterpart International Application No. EP 03 425 106.6 (4 pages).

RD 434009A, published Jun. 10, 2000, entitled "Therapeutic Agent Loading Device for Stents Comprises Anchor Inserted in Stent Coated with Therapeutic Agent Specific Binding Polymer and Rolled on Carrier Soaked with Therapeutic Agent" (7 pages).

* cited by examiner

Fig_1

Fig_2

Fig_3

Fig. 12

PROCESS FOR PRODUCING STENTS AND CORRESPONDING STENTS

This application is a continuation of application Ser. No. 10/782,412, filed Feb. 19, 2004, the contents of which are hereby incorporated by reference herein.

The present invention relates to stents. Stents are expandable endoprostheses that can be implanted in a lumen of the human body or animal body, such as a blood vessel, for re-establishing and/or maintaining the patency thereof. Stents are usually configured as devices of a tubular shape which operate so as to maintain open a segment of a blood vessel or of another anatomic lumen. Stents have become widely used over the last few years for the treatment of stenosis of an arteriosclerotic nature in blood vessels such as coronary arteries. Stents are now being used in other regions of the body such as the peripheral regions.

The scientific and technical literature, including the patent literature, regarding stents is quite extensive. For example, the following documents relate to stents: EP 0 806 190 A1, EP 0 850 604 A2, EP 0 875 215 A1, EP 0 895 759 A1, EP 0 895 760 A1, EP 1 080 738 A1, EP 1 088 528 A1, EP 1 103 234 A1, EP 1 174 098 A2, EP 1 212 986 A1, and EP 1 277 449 A1.

The activities of research, development and industrialization of stents were directed, in the early years, principally to the geometrical structure and to the corresponding techniques of fabrication (winding of a wire, cutting from a microtube, use of superelastic materials, etc.). The research activity regarding stents then gradually extended to other specific embodiments, and in particular to the possibility of applying on stents or of associating to stents pharmacological agents. Such pharmacological agents are able to perform a specific activity at the implantation site of the stent. Drugs that have a restenosis-antagonist action are of particular interest.

For example, EP 0 850 604 A2 describes the possibility of providing the stent with a sculpture that comprises, for instance, recesses that may receive one or more drugs that are useful in the prevention or treatment of restenosis and/or other substances that are expedient for ensuring proper use of the stent (adhesion, mode of release, kinetics, etc.). The surface sculptures are characterized both by the outline and the surface of the recess, and by the depth profile. For example, the recesses may be cavities having circular or else ovoidal or again elongated openings. Alternatively, they can assume the form of an appropriate alternation of cavities with openings of different types according to the needs of release. The depth profile may be U-shaped or V-shaped, or shaped like a vessel with or without a surface part completely dedicated to the reception of the substances in question referred to above. The surface part may assume the appearance of a sort of continuous layer on just the outer surface of the stent.

In the course of the last few years, extremely extensive activity has been dedicated to developing materials, particularly pharmacological agents, to be loaded on the stent. The material to be loaded on the stent may consist of just one drug, of a pair of drugs, or of an ensemble of drugs with similar, synergetic, or different actions. In addition to pharmacologically active molecules, the stent can serve as a vehicle for substances having the function of adjuvant of pharmacologically active substances, such as polymers or excipients of various natures. The function may be of stabilization of the active substance or active substances, or else be aimed at regulating the kinetics of release (deceleration or acceleration of release). The polymers/excipients can be mixed with the drug or drugs or else are in separate layers with respect to the pharmacologically active substances. For example, a recess in the stent could contain a sort of bioerodible-polymer plug or the material on the stent could have a stratified structure with successive layers of drug and polymer.

Even though in scientific circles this type of application is not considered at the moment particularly attractive, the character of activity of the substances loaded on the stent may include substances that are of a radioactive nature.

The scientific and patent literature relating to materials to be loaded on the stent is extremely extensive, as is witnessed, not only by some of the documents already cited previously, but also by documents such as, for example: EP 0 551 182 A1, EP 0 747 069 A2, EP 0 950 386 A2, EP 0 970 711 A2, EP 1 254 673 A1, EP 1 254 674 A1, WO 01/87368 A1, WO 02/26280 A1, WO 02/26281 A1, WO 02/47739 A2, WO 02/056790 A2 and WO 02/065947 A2, as well as by the literature cited in these documents. These documents and literature, it may be added, by no means exhaust the field.

As regards the choice of drug having restenosis-antagonist function, the drugs known as rapamycin (sirolimus) and FK506 (tacrolimus) have assumed particular importance.

The problems linked to the use of drugs on the stent are not moreover limited to the choice alone, i.e., to the identification of the substance or substances used, but involve various other aspects. Among these further aspects are: (i) the physical form of the substances to be loaded; (ii) the technique of loading of the material; (iii) the technique of cleaning of the excess material deposited; and (iv) the stabilization of the material itself.

The techniques of loading should take into account the nature (i.e., the physical form) of the substance or substances loaded on the stent. Some techniques of loading of a known type basically operate in an indirect way in so far as they substantially envisage the formation of a coating on the stent, typically one of polymeric material (for example polymers of methacrylate, polyurethane, PTFE, hydrogel or hydrogel/polyurethane mixture, especially PTFE), to which the drug to be applied on the stent is linked and/or in which it is dissolved before application of the coating, subsequently designed to be stabilized by polymerization. Other techniques substantially envisage, instead, starting from agents in liquid form or low-viscosity solutions or dispersions. This method is used because in the majority of cases considered because the drugs in question are available in the market in the form of a powder (of different grain size).

The simplest solution envisages loading the stent by dipping it in a carrier, typically a liquid, in which is dissolved, suspended or anyway present the substance or substances to be loaded on the stent. This technique, which may possibly be conducted in vacuum conditions, is referred to in the art as "dipping". For example, the document WO 02/065947 A2 describes a solution in which the stent is brought into contact with a solution of FK506 in aqueous or organic solvent (typically in an alcohol, such as ethanol, in a concentration of 3.3 mg of FK506 in 1 ml of ethanol). This takes place, for example, by dripping, spraying or dipping, preferably in vacuum conditions. The stent is then dried, preferably enough to remove the solvent. The drug coating operation preferably is then repeated from one to five times. Subsequently, the stent is possibly washed one or more times with water or isotonic saline solution, and may then possibly be dried.

The known methods described above, albeit satisfactory, come up against a wide range of drawbacks. Among these are: (i) the complexity of the operation of loading; (ii) the need, in the case where a coating is made on the stent, in which the drug to be applied on the stent is bound and/or dissolved, to take into account the characteristics of the coating and the possible subsequent elimination thereof; (iii) the difficulty of obtaining selective coatings, i.e., ones limited to well-confined areas of the stent; (iv) the difficulty of loading, with a limited number of steps, a plurality of different agents; and (v) the difficulties that are intrinsically linked to the simultaneous loading of a number of agents and possible excipients or other substances that may contribute to the control of the kinetics of release.

The purpose of the present invention is to overcome the drawbacks pointed out above, paying particular attention to its possible use for making stents with associated biologically active substances, i.e., the so-called "bioactive stents". The above mode of use regards in particular the possible presence on the stent of at least one drug which may perform a restenosis-antagonist function, such as for example FK506. According to the present invention, the above purpose is achieved thanks to a process having the characteristics described below. The invention also regards the corresponding stent.

In summary, the invention envisages carrying out the loading operation starting from a powder or from a paste obtained from the powder itself. It will be appreciated that the term "paste" is here understood to indicate any plastic mass having a degree of viscosity such as to ensure that the mass will substantially preserve its shape if exposed only to the force of gravity. This definition is in evident contrast with a liquid or cream, which do not demonstrate these characteristic of preservation of shape. The existence or else absence of this characteristic may be determined in a simple way by depositing on a surface a mass of substance in an amount corresponding to the quantity required for the applications here considered and verifying whether the mass preserves or else modifies its shape as a result of the force of gravity.

The powder or paste here considered may consist of: (i) a pure drug; (ii) a mixture of two or more drugs in appropriate proportions; and (iii) a mixture of drugs, excipients and/or substances (such as polymers) that contribute to the control of the kinetics of release.

Preferably, the drug is FK506, i.e., the macrolide antibiotic FK506 (tacrolimus, [3S-[3R*[AND(1S*,3S*,4S*)],4S*, 5R*,–8S*,9E,12R*,14R*, 15S*,16R*,18S*,19S*,26aR*]]-5,6,8,11,12,13,14,15, 16,17,18,19,24,25,25,26a-hexa-decahydro-5,19-dihydroxy-3-[2-(4-hydroxy-3-methoxycyclohexyl)-1-methylentenyl]-14,16-dimethoxy-4, 10,12,18-tetramethyl-8-(2-propenyl)-15,19-epoxy-3H-pyrido[2,1-c][1,4]oxaazacyclotricosin-1,7,20,21(4H,23H)-tetrone; Merck index No. 9000). This drug is an active substance originally developed for the medicine of transplants and the immunosuppressive action of which extends evidently also to the restenosis-antagonist mechanism.

Drugs presenting characteristics that are on the whole similar, which can be used in association with, or alternatively to, FK506, are: cyclosporine, leflunomide, mycophenolate, brequinar, rapamycin, everolimus, ABT-574 or other derivatives of rapamycin; PDGF antagonists; paclitaxel or 7-hexanoyl-taxol; cisplatin; vinblastin; mitoxantrone; combretastatin A4; topotecan; methotrexate; flavopyridol; actinomycin D; rheopro/abciximab or probucol, and drugs capable of mitigating or preventing reactions underlying the process of restenosis, such as: rapamycin, heparin and the like, actinomycin D, batimastat, paclitaxel, resten NG (oligonucleotide), and dexamethasone.

Drugs that can be advantageously combined with FK506 and/or other drugs with restenosis-antagonist action, or else, in general, drugs that can be loaded on a stent according to the modalities herein described include the following.

Drugs with anti-inflammatory action, such as:
Corticosteroids,
Cortisol Betamethasone Fluocinolone,
Cortisone Dexamethasone Fluocinonide,
Corticosterol Flunisolide Fluoromethalone,
Tetrahydrocortisol Alclomethasone Flurandrenolide,
Prednisone Amcinonide Alcinonide,
Prednisolone Clobetasol Medrisone,
Methylprednisolone Clocortolone Momethasone,
Fluodrocortisone Desonide Rofleponide,
Triamcinolone Desoxymethasone,
Paramethasone Diflorasone,
as well as all the corresponding esters, salts and derivatives.
 Non-steroidal anti-inflammatory drugs (NSAIDs):
Salicylates: Acetylsalicylic acid,
Diflunisal,
Salsalate,
Pyrazolones: Phenylbutazone,
Oxyphenbutazone,
Apazone,
Indomethacin,
Sulindac,
Mephenamic acid and phenamates,
Tolmetin,
Derivatives of propionic acid: Ibuprofen,
Naproxen,
Fenoprofen,
Ketoprofen,
Flurbiprofen,
Pyroxicam and derivatives,
Diclofenac and derivatives,
Etodolac and derivatives,
 Drugs with anti-neoplastic action:
Alkylating agents:
Nitrogenated mustards: Cyclophosphamide,
Melfalan,
Chlorambucyl,
Ethylenimin and methylmelamine,
Alkyl sulphonates,
Nitrosureas: Carmustin,
Triazenes,
Antimetabolites:
Analogues of Folic acid: Methotrexate
Analogues of Pyrimidines: Fluorouracyl
Analogues of Purines and derivatives: Mercaptopurine,
Thioguadinine.
 Natural Products:
Vinca alkaloids: Vinblastine,
Vincristine,
Epipodofillotoxines: Ethoposide,
 Antibiotics: Actinomycin D,
Doxorubicin,
 Various:
Complexes of Platinum: Cisplatinum,
Mitoxantrone and derivatives,
Hydroxyurea and derivatives,
Procarbazine and derivatives,
Mitotanes,
Aminoglutetimide,
Derivatives having a naphthopyranic structure,
Derivatives of butyric acid,
Taxanes: Taxol,
Docetaxel,
Epotilones,
Batimastat and analogues,
Drugs with action promoting processes for repairing the vessel wall,
Endothelial/angiogenetic growth factors: e.g., VEGF or antisense
 oligonucleotides, Antisense oligonucleotides: e.g., antisense c-myb,
Prostacyclin and analogues: Ciprostene,
Dipyridamol,
Calcium blockers,
Arylalkylamines: Diltiazem, Verapamyl, Fendiline, Gallopamyl, etc.,
Dihydropyridines: Amlodipine, Nicardipine, etc.,
Piperazines: Cinnarizine, Lidoflazine, etc.,
Colchicines,
  Drugs that act on c-AMP:
Aminofilline, IBMX (bronchodilators),
Anrinone (cardiotonic),
8-Bromo-c-AMP and c-AMP analogues,
  Drugs that act on the lipid metabolism:
Statins: simvastatin, fluvastatin, etc.,
Unsaturated ω-3 fatty acids,
Somatostatin and analogues: Sandostatin, Angiopeptin, etc.
Cytocalasines,
Etretinate and derivatives of retinoic acid,
  Anticoagulants: Irudin, Heparin and derivatives,
Trapidyl: vasodilator,
Nitrogen monoxide and its generators: Molsidomin,
  Antiplatelet agents: Ticlopidin, Dipyrimidamol, etc.,
  Agents that can act on the activity of the cell and on the regulation of the cell matrix:
protein (elafin),
oligonucleotides,
genes,
RNA, DNA and fragments,
RNA, DNA and antisense fragments,
Monoclonal antibodies.

For each active substance cited herein, including the active substance FK506, the concept of "active substance" also covers direct derivatives of the active substance, and the active substance also in all the types of salts, enantiomers, racemic forms, bases, or free acids of the active substance, and their mixtures.

It will moreover be appreciated that, rather than to the identification of the specific substance applied on the stent, the present invention directs its main attention to the technique (rheology) of application thereof. The application in the form of a powder or of a paste formed from the powder manages to reconcile the need for making a selective application (an important factor both for the purposes that it is intended to pursue and for the costs of the substances applied, which are usually rather high), with the need of ensuring the firm retention of the substances applied on the stent.

The above result has been obtained without complex operations of loading, and avoids the need to make on the stent a coating in which the drug to be applied on the stent is bound and/or dissolved. The invention provides a method of obtaining with relative ease selective coatings, i.e., coatings limited to well-confined areas of the stent, and/or of loading a plurality of different agents, while avoiding the difficulties that are intrinsically linked to the simultaneous loading of a number of agents and possible excipients or other substances that may contribute to controlling the kinetics of release.

Usually, the result of the process of loading must be selective, in the sense that it must load only those areas of the stent that actually have to carry the drug or drugs, as well as the possible additives (excipients). Of course, this result can be achieved also passing through a generalized loading, which initially loads also areas of the stent that are designed to be subsequently cleaned to remove the excess substances loaded.

Once the substances chosen have been deposited on the stent (before or after cleaning, according to the operative choices or techniques adopted), the next step is fixation of the drug or drugs, as well as of the additives. The purpose of this is to ensure that the substances can be effectively transported by the stent onto an implantation site and not be dispersed elsewhere, in particular during advance towards the implantation site or even before the stent is inserted in the body in which it is to be implanted. The operations of stabilization can be conducted in a selective way on the sole parts where the presence of the substances deposited is required or else in a generalized way over the entire stent, at least as regards the outer surface thereof.

In a specific way, in the case where the starting part is a powder, the main methods of loading that can be adopted are: (i) recourse to a non-selective corona effect (electrostatic effect), i.e., coating the entire surface with powder and then cleaning the areas that require cleaning; (ii) recourse to a selective electrostatic process (such as photocopier or laser printer), for example through an intermediate roll that collects the powder only in areas corresponding to the recesses, in which it deposits it subsequently; if they are stents with the entire outer surface porous, selectivity is in general not required, and, in both of the cases so far considered, no specific cleaning operation is called for; (iii) rolling on a bed or mat of powder, with subsequent cleaning; and (iv) rolling on a bed or mat of powder with a mask of a serigraphic type so as to load the recesses alone; no cleaning is required.

In the case where the starting point is paste, the main methods of loading usable are: (i) rolling on a bed or mat of paste, with subsequent cleaning; (ii) rolling on a bed or mat of paste with a protective mask (serigraphy); cleaning is not required; and (iii) application with a dispensing nozzle, typically moved by a numerical control machine for fine positioning.

It will moreover be appreciated that whatever the loading procedure adopted, either for paste or for powder, it is then preferable to proceed to a stabilization operation, where by "stabilization" gives the content of the cavity a mechanical quality and a degree of adhesion to the recesses themselves adequate for the mechanical stress exerted on the stent in the steps of transportation, storage, procedure, and expansion.

To achieve the desired effect of stabilization, it is possible to resort to techniques, such as: (i) exposure to temperature or thermal cycles; (ii) dipping in solvent for controlled lengths of time; (iii) exposure to solvent spray; (iv) exposure to solvent vapors; (v) selective treatment with laser (exposure of the recesses to the laser beam); (vi) selective or integral application of a protective adhesive coating (in the form of a plug for closing the recesses); and (vii) lyophilization.

The invention will now be described, purely by way of non-limiting example, with reference to the annexed drawings.

The present description is provided, purely by way of non-limiting example, with reference to a stent 1 substantially corresponding to the stent described in U.S. Pat. No. 6,325, 821 B1, the contents of which are hereby incorporated by reference herein. Such a stent consists of a tubular body made of metal material, which may be dilated, starting from a radially contracted condition to a radially expanded condition. The body of the stent comprises a plurality of structural elements or struts 10, which define a structure with openings presenting an on the whole reticular character.

In particular, in the solution described in U.S. Pat. No. 6,325,821 B1 the structure in question comprises a plurality of annular segments arranged in succession along the longitudinal axis of the stent. The segments in question present a serpentine pattern with loop-like parts arranged in opposite sequence, connected together by connection elements (commonly referred to as "links"). The serpentine sequences of the successive segments are usually in phase opposition, i.e., with a concavity of each serpentine opposite to a concavity of an adjacent segment. The connection elements present a substantially V-shaped pattern with a profile characterized by an alternation of concave portions and convex portions. The aforesaid connectors connect the various annular segments of the stent at the "0" points or nodes of the serpentine paths of the segments.

In the view presented in the attached drawings, the stent 1 is represented in cross section, so that in the drawings only the circular trace of the cross section is perceptible, which is defined by a certain number of struts traversed by the cross-sectional plane. The stent in question is provided, on its outer surface, with a sculpture formed by a pattern with recesses 12 of the type described in U.S. Pat. No. 6,638,302 B1 or U.S. Patent Application Publication No. 2003/0028242 A1, the contents of each of which are hereby incorporated by reference herein. The recesses 12 can receive within them respective masses 14 of a material comprising an active substance, such as FK 506 and/or any one of the other substances or combinations of substances to which ample reference has been made previously.

In a particularly advantageous way, the stent in question is coated, on its outer surface, with a layer of biocompatible carbon material deposited thereon by resorting to the technique described, for example, in U.S. Pat. Nos. 5,084,151, 5,133,845, 5,370,684, 5,387,247, and 5,423,886, the contents of each of which are hereby incorporated by reference herein. The presence of the coating of biocompatible carbon material proves advantageous for the purposes of use of the stent, in particular as regards the minimization of the effects resulting from the implantation of the stent. The presence of the coating of biocompatible carbon material proves likewise advantageous for the purposes of loading of the stent, which is performed with the processes of an electrostatic type described in greater detail in what follows.

General Loading Technique

Figure 1:
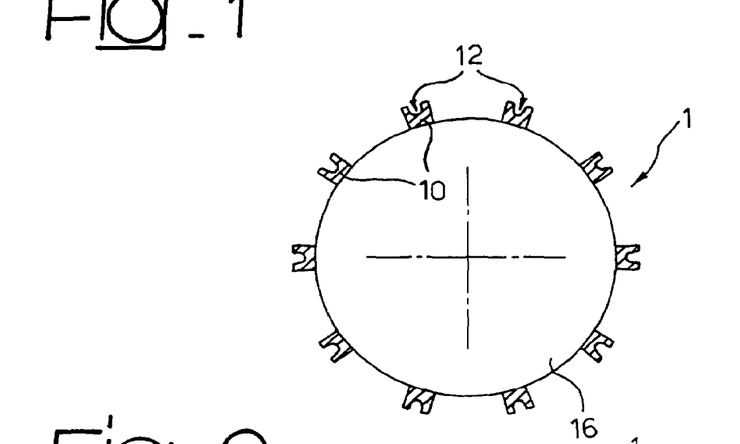
FIGS. 1 to 3 illustrate, in general terms, the operation of loading of a drug or of another substance in the form of powder or paste on a stent.
Figure 2:
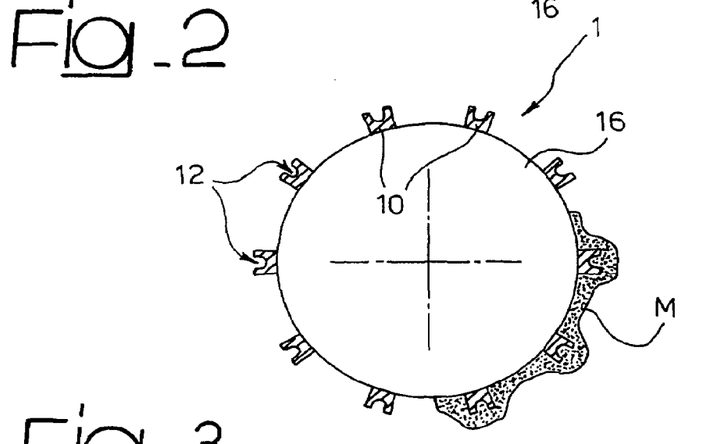
Figure 3:
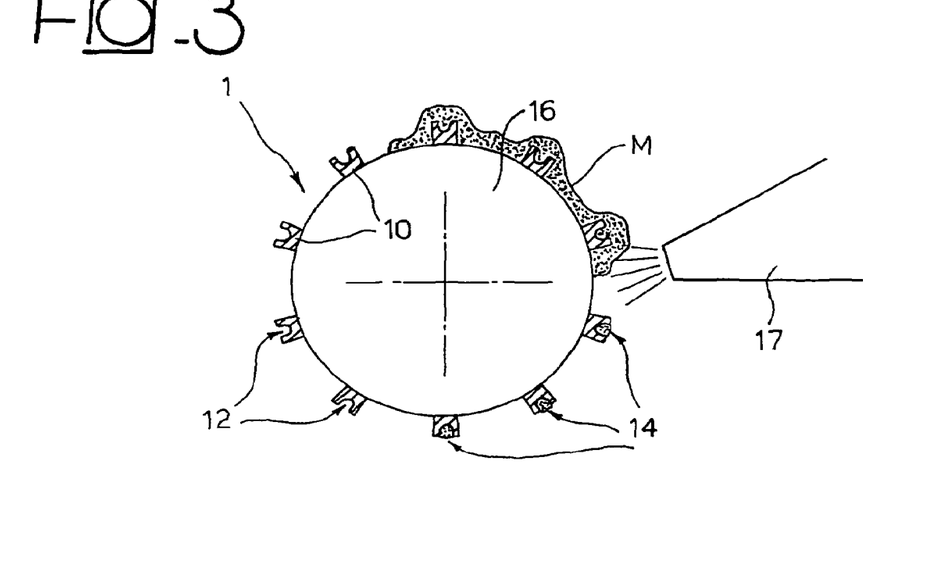

FIGS. 1 to 3 of the annexed drawings illustrate the technique here described in its more general terms. The stent 1 is usually mounted on a support or spindle 16 designed to enable its manipulation (also by means of a mechanical manipulator, which may possibly be automatic) without risks of damage. The stent can be treated both in a radially expanded condition, and in a radially contracted condition. The treatment in a radially contracted condition is, however, preferred in that it facilitates the operations of manipulation and cleaning. Tests show that the radial contraction of a stent loaded in a radially expanded condition leads to a modest compacting of the substance loaded in the recesses 12, which acts in a synergetic way with the stabilization of the substance itself.

FIG. 2 illustrates the operation whereby (according to different modalities, described in greater detail in what follows) the substance M designed to be loaded in the recesses 12 is applied, in the form of a powder or a paste, on the surface of the stent 1. In particular, FIG. 2 refers to an operation of application performed in a non-selective way, i.e., ensuring that the substance M not only fills the recesses 12, but covers instead the surface of the stent 1 in a practically complete way.

FIG. 3 illustrates the subsequent cleaning operation, in which the substance M in excess is removed. For example the substance M can be removed by using a localized jet of fluid coming from one or more nozzles 17 so as to leave only the specific dose 14 inside the recesses 12.

EXAMPLE 1

Non-selective Electrostatic Loading with Powder

Figure 4:
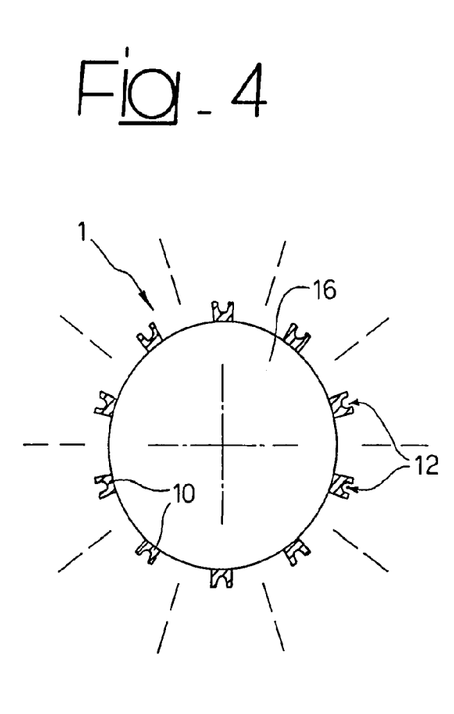
FIGS. 4 to 6 are schematic illustrations of the loading operation performed with an electrostatic process (corona effect) of a non-selective type.
Figure 5:
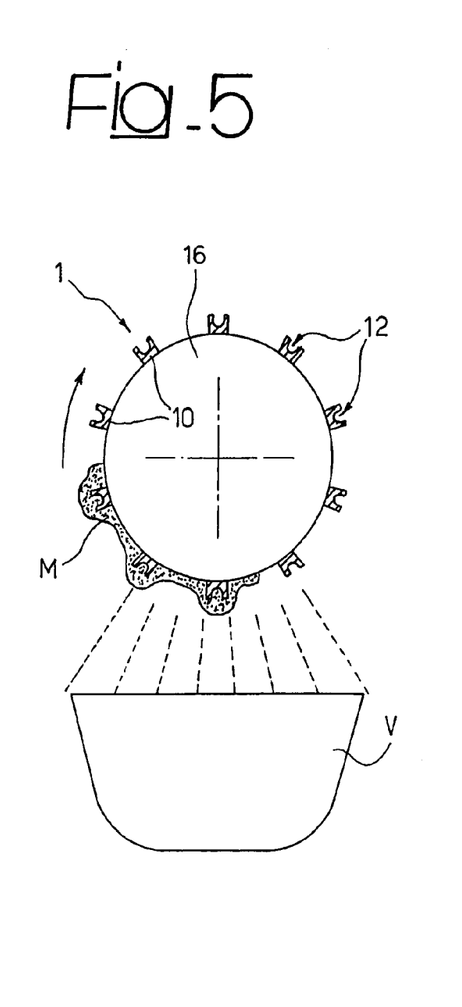
Figure 6:
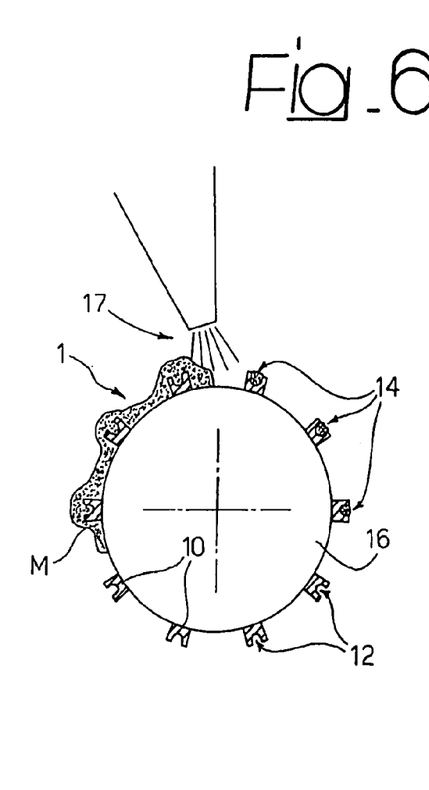

A very fine powder, with a typical grain size of less than 15 micron, of drug FK 506 (tacrolimus) is laid in a thin and level layer inside a tray V. The stent 1 is positioned on a support 16 capable of being charged electrostatically, for example as a result of a corona treatment of the type currently performed on the printing rolls of photocopier machines (FIG. 4). The support 16 is electrostatically charged, and the support 16/stent 1 ensemble is made to rotate (FIG. 5) at a distance of a few tenths of a millimeter from the surface of the powder that is in the tray V. The drug M is attracted over the entire surface of the support/stent ensemble and adheres in a uniform way to the stent, also filling its cavities 12. The next step is to remove the excess of drug M from the areas other than the recesses 12. For this purpose, the stent 1 still fitted on its support 16 is cleaned by a sequence of jets of cold water and of nitrogen under pressure shot from one or more nozzles 17 appropriately positioned around the stent (FIG. 6). Alternatively, the stent 1 is fitted on a nozzle comprising a perforated tube and is impinged upon by a short sequence of jets of cold water, emitted under pressure from inside the stent. The jets of water are interspersed with puffs of nitrogen under pressure. The remaining residue is removed from the outer surface of the stent thanks to the rubbing of the latter against a second support, e.g., a cylinder with a compliant, i.e., soft surface.

To stabilize the drug in the sculptures (recesses) 12, the stent that has been loaded is subjected to a spray of solvent effective on FK506, such as for example acetonitrile, from a distance of 15 cm, or else exposed to acetonitrile vapors in a chamber for thin-layer chromatography for 5 minutes.

EXAMPLE 2

Selective Electrostatic Loading with Powder

Figure 7:
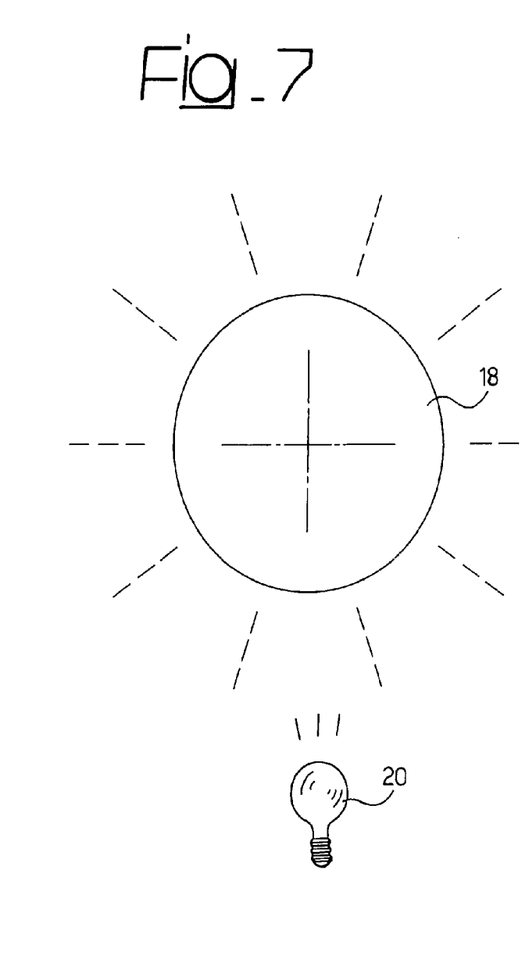
FIGS. 7 and 8 are schematic illustrations of the loading operation performed with an electrostatic process of a selective type.

As in the case of the previous example, a very fine powder of the drug FK506 (tacrolimus), with the same grain size as in Example 1, is laid in a thin and level layer inside a tray V. A roll 18 coated with photosensitive material capable of being charged electrostatically is exposed to a light source 20 capable of activating or de-activating in a selective way (from the standpoint of electrostatic charging) areas of the surface of the photosensitive roll 18 according to a geometry corresponding to the geometry of the recesses 12 (FIG. 7). The final result is the presence, on the surface of the roll 18, of a distribution of electrostatic charges that reproduces the distribution of the recesses 12 on the surface of the stent.

Figure 8:
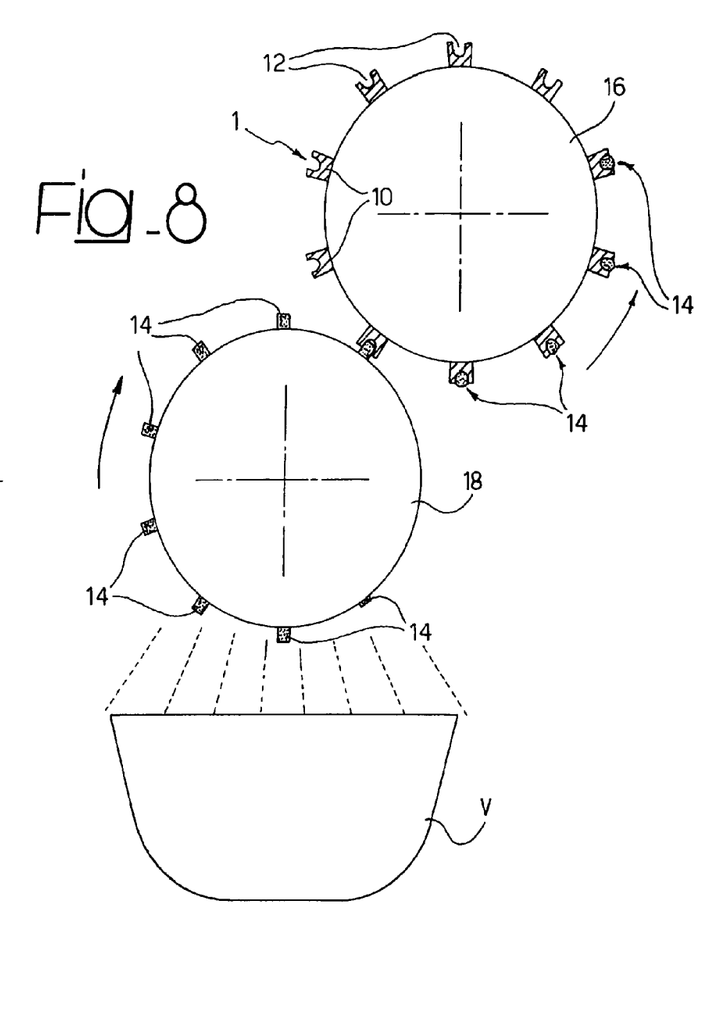

Then, by passing over the bed of powder that is in the tray V, the roll 18 carries away with it masses 14 of drug M, the distribution and shape of which correspond to those of the recesses 12 (FIG. 8). The roll 18 is then used (like an offset roll in a similar printing process) for transferring the masses 14 into the recesses 12 of the stent 1 mounted on the support 16 (this also usually being charged electrostatically) (FIG. 8).

The drug M is deposited on the stent 1, which turns in an opposite direction alongside the roll 18, in areas corresponding to the sculptures or recesses 12. When all the recesses or sculptures of the stent are loaded with the drug, the next step of the process is the fixation of the substance according to the procedure already described previously (acetonitrile vapors in a thin-layer chromatography chamber for 5 minutes).

It will be appreciated that the process just described, in addition to not requiring the step of cleaning of the excess drug, lends itself also to being repeated with different substances, for example so as to fill different recesses with different drugs. In particular the operations of: (i) subjecting the roll 18, functioning as support for transfer of the active substance M, to a charging treatment designed to obtain electrostatic charging of respective regions that are homologous with respect to the recesses 12 of the surface of the stent 1, (ii) exposing the roll 18, with the aforesaid respective electrostatically charged regions, to the active substance M that is in the tray V, ensuring that the electrostatic charge will cause transfer of the active substance onto the electrostatically charged regions of the roll 18, and (iii) exposing the roll with the active substance M, transferred onto said respective electrostatically charged regions, to the surface of the stent 1, said exposure determining the transfer of the active substance M into the recesses 12 of the stent 1, each can be repeated by employing active substances M that are each time different, with the respective electrostatically charged regions of the roll 18 chosen so that they are either identical or different for the various active substances used.

As has been mentioned previously, the presence, at least on the outer surface of the stent 1, of a coating of biocompatible carbon material proves advantageous for the purposes of loading the stent performed according to the processes of an electrostatic type described in Examples 1 and 2.

Examples 1 and 2 set forth previously can also be implemented using a paste and not a powder. In this case, the transfer of the substance M onto the electrostatically charged areas of the stent 1 or of the roll 18 usually presupposes an at least marginal contact and not only the close proximity between the substance M and the stent 1 or the roll 18.

EXAMPLE 3

Rolling on a Bed or Mat of Paste

A mixture of drug FK506 (tacrolimus) with glycerine is prepared by amalgamating the powder of Example 1 with a few drops of glycerine. The paste thus obtained, indicated by M, has a viscosity that is hard to determine but can be estimated to have a lower limit of 100,000 to 120,000 cps.

Figure 9:
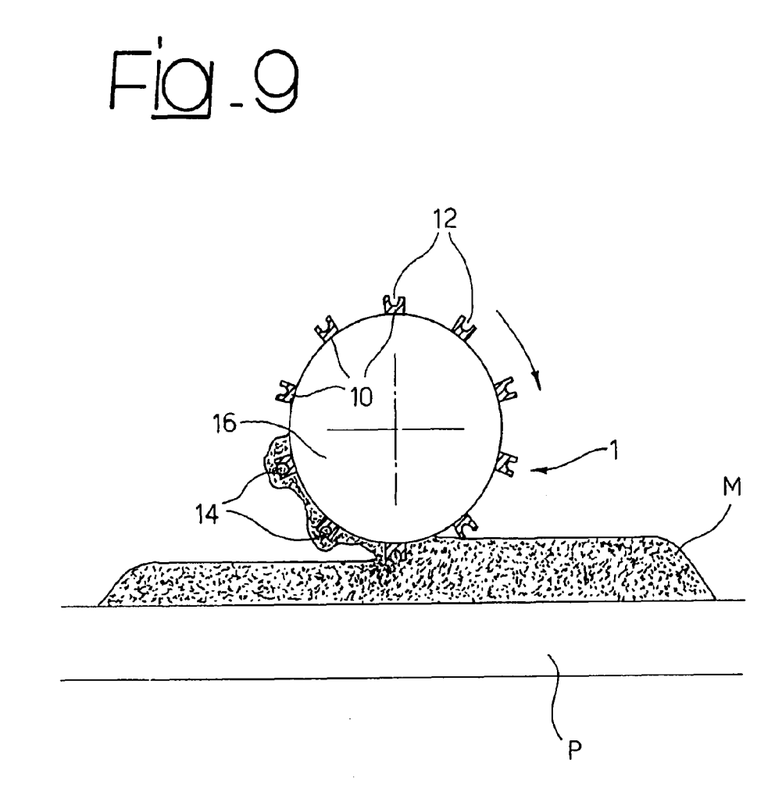
FIGS. 9 to 11 are schematic illustrations of the loading operation performed with a process of rolling on a bed or mat.

The paste M is then deposited and spread out over a surface P, such as for example the bottom of a tray (not illustrated), so as to form a uniform bed or mat. The support 16 for the stent is mounted so as to be able to rotate with respect to its longitudinal axis and an axis to translate along the tray itself-on a track. By means of the movement of rotation and translation, accompanied by a certain pressure, the outer surface of the stent comes into contact with the paste M, and a layer of paste P is deposited on the outer surface of the stent and fills the recesses 12 (FIG. 9).

Figure 10:
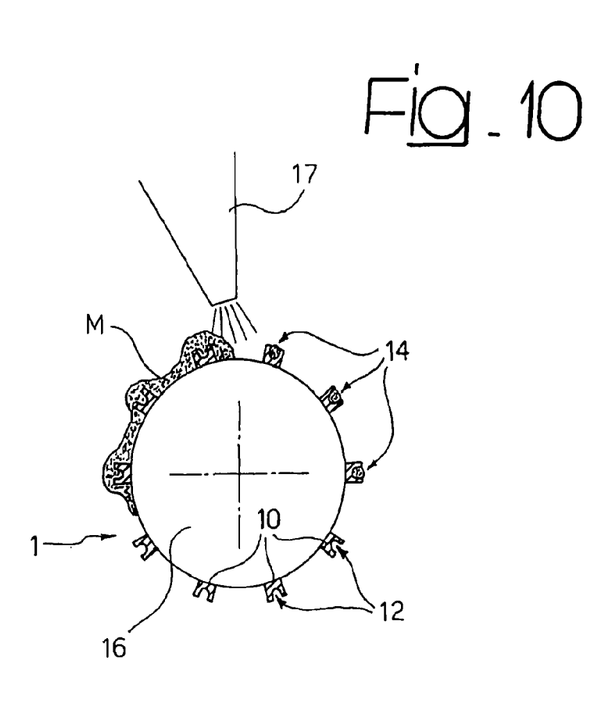

Tests show that, at least for some ranges of viscosity and of adhesiveness of the paste (parameters that depend of course upon the nature and upon the quantity of components), the phenomenon of transfer of the paste on the stent 1 involves, in a practically exclusive way, the recesses 12, which evidently exert a sort of action of "capture" on the paste. After having possibly removed the fractions of paste M that have remained adherent to the regions of the surface of the stent other than the recesses 12 (FIG. 10), the stent 1 itself is then removed from the support 16 and left to rest at room temperature (e.g., for a period not shorter than 6 hours).

To render homogeneous and intimately adherent, i.e., to stabilize, the drug-glycerine mixture on the surface of the sculptures, the stent is subsequently exposed to vapors of ethyl alcohol in a thin-layer chromatography chamber. Exposure is performed for 5 minutes at 30° C. The stent is then left to dry for 6 hours, dipped for 15 seconds in water, and again left to dry for 24 hours. In a less preferred way, the operation of removal of the fractions of paste M that remain adherent to the regions of the surface of the stent other than the recesses 12 may possibly follow the operation of stabilization, instead of preceding it.

EXAMPLE 4

Rolling on a Bed or Mat of Paste

A mixture of drug FK506 (tacrolimus) and of polycaprolactone in the form of powder (in a ratio of 6:4) is prepared by amalgamating the powder with a few drops of ethyl acetate. Also in this case, the paste thus obtained, designated by M, has a viscosity that is hard to determine but can be estimated to have a lower limit of 100,000 to 120,000 cps.

As in the case of Example 3, the paste M is then deposited and spread out over a surface P, such as for example the bottom of a tray (not illustrated), so as to form a uniform bed or mat. Once again in a way similar to what was seen in the case of Example 3, the support 16 for the stent is mounted so as to be able to rotate with respect to its longitudinal axis and translate along the tray itself on a track, applying to the stent a certain pressure in the direction of the bed of paste M.

Figure 11:
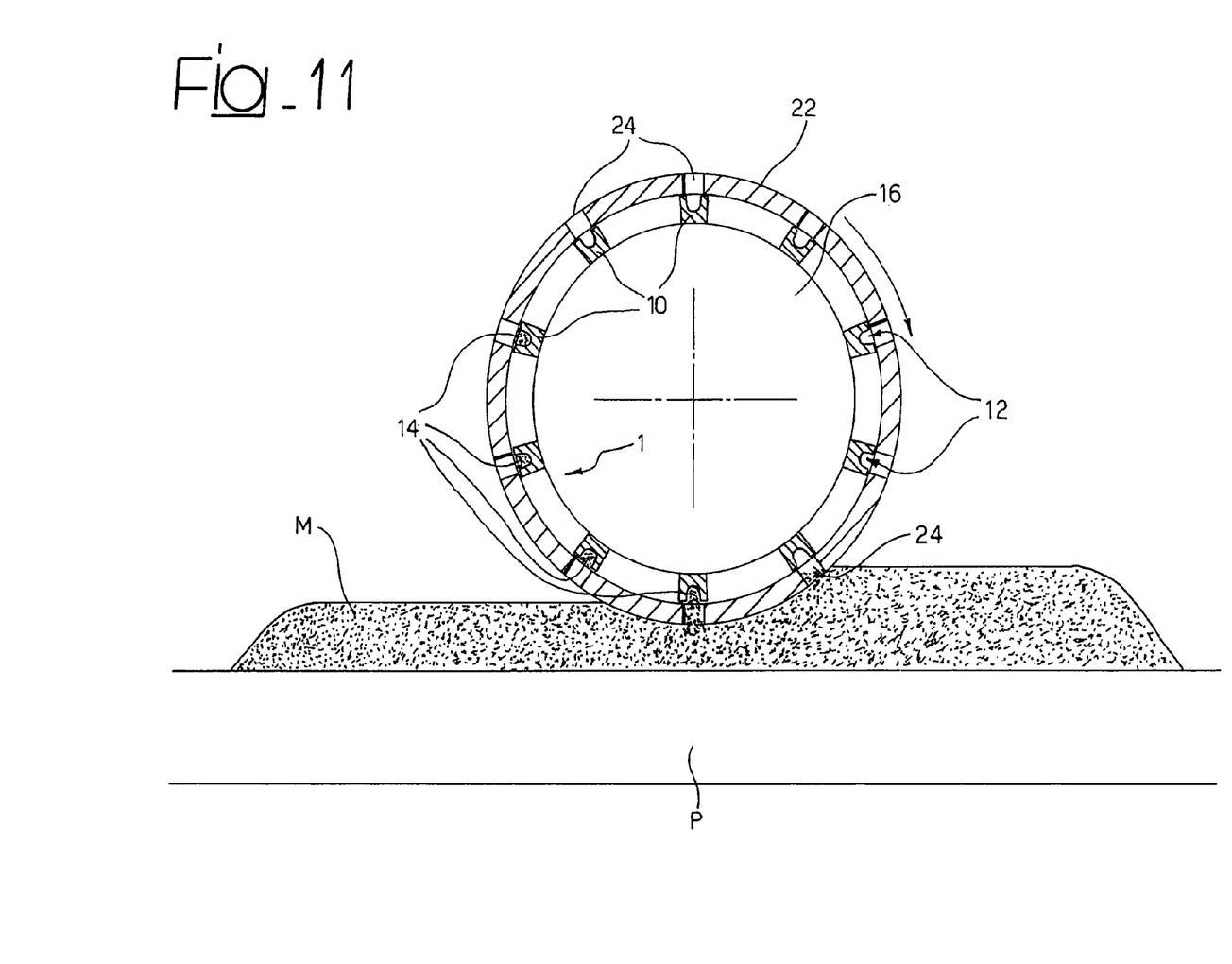

Applied on the stent, mounted on the support 16, is a mask 22 consisting of a metal cylinder with slits 24 the geometry of which corresponds to the geometry (number, shape and position) of the sculptures or recesses 12 present on the outer surface of the stent (FIG. 11). The diameter of the mask 22 is chosen so that, once fitted on the stent 1, the mask 22 will adhere perfectly to the outer surface thereof, leaving free only the required recesses 12. Also in this case, the movement of rotation and translation of the support 16/stent 1/mask 24 ensemble on the tray containing the paste M enables deposition of a layer of paste M on the outer surface of the mask 24 and in the recesses 12 of the stent 1 that are left free by the openings 24 of the mask 22.

At this point, the next step is the fixation of the drug-polymer mixture to the surface of the stent 1/mask 22 ensemble, for example by putting everything in a stove at 65° C. for 15 minutes. Once cooled, the stent 1 is released from the mask 22 and slid out of the support 16.

It will be appreciated that this technique lends itself to repetition with different masks and different substances, so as to fill different recesses with different drugs. Specifically, the process of Example 4 seen previously can be conveniently implemented, as follows: (i) applying on the stent 1 a first mask 22 with first openings 24 that leave uncovered first regions or recesses 12 of the stent 1; (ii) exposing the stent 1, with the first mask applied thereto, to the bed of active substance M, so that the active substance M will coat the mask 22 and the first regions 12 left uncovered by the openings 24 of the first mask 22; (iii) removing the first mask 22 from the stent 1, which is covered with the active substance in areas corresponding to the (first) regions or recesses 12 seen previously; (iv) applying on the stent 1 a second mask 22 with second openings 24, which leave uncovered second regions 12 of the stent (these may coincide at least in part with the regions 12 already coated); (v) exposing the stent 1, with the second mask applied thereto, to a bed of further active substance M (usually different from the one seen previously), so that said further active substance will coat the second mask 22 and the second regions or recesses 12 left uncovered by the openings 24 of the second mask 22; and (vi) removing the second mask 22 from the stent 1, which has thus been loaded with different substances in regions that are different or coincide with one another, according to the needs.

Examples 3 and 4 described previously are suited to being implemented with a bed or mat of substance M in the form of powder and not in the form of paste.

EXAMPLE 5

Figure 12:
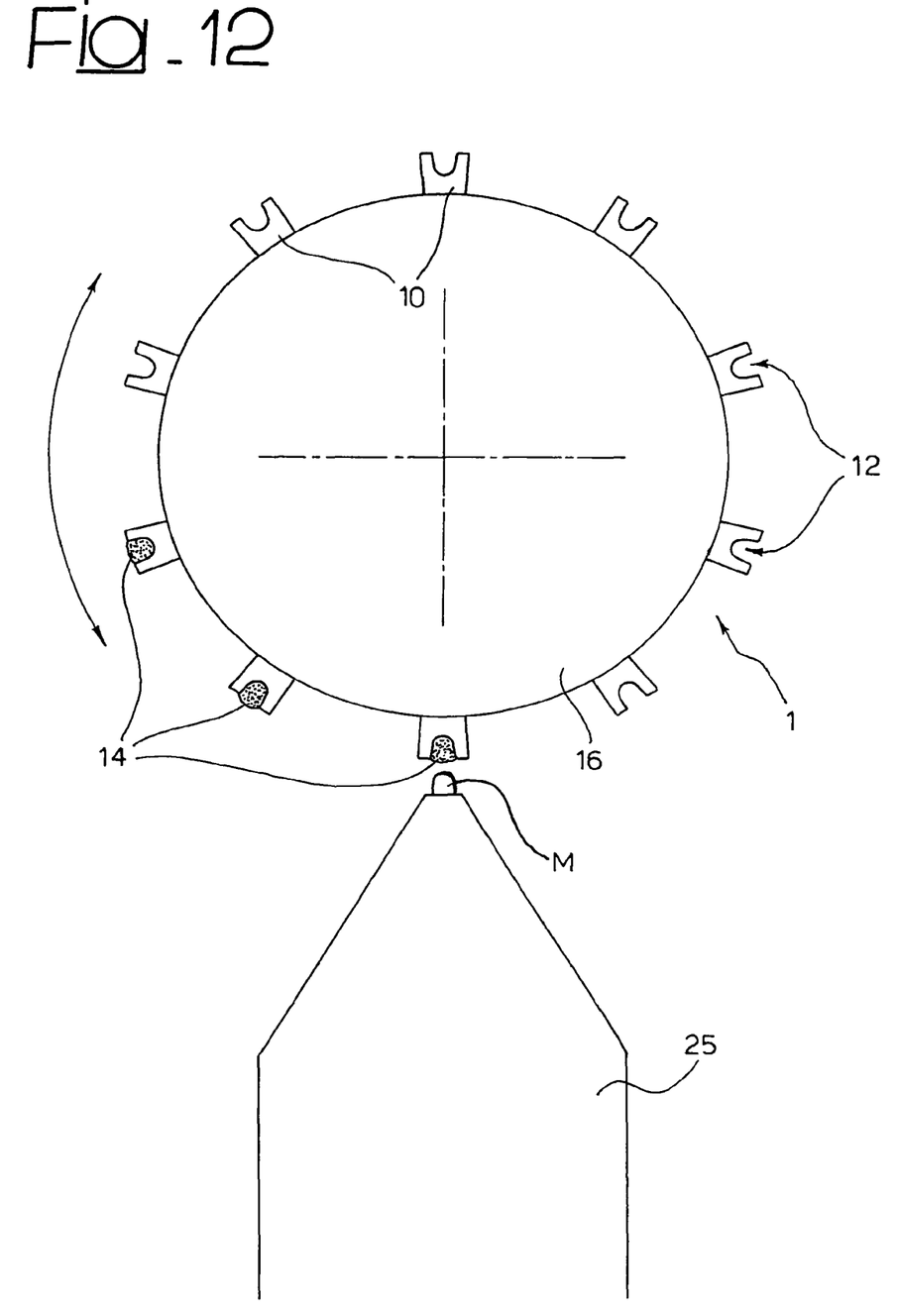
FIG. 12 illustrates the implementation of the loading operation by a device for dispensing a paste.

Finally, FIG. 12 refers to the possibility of applying selectively only inside the recesses 12, respective masses 14 of material in the form of paste. This is achieved by means of a dispensing nozzle 25 which may be brought into a position facing the recesses 12, then imparting on the recess 12 each time involved and on the nozzle 25 a relative movement that leads the nozzle to "scan" the recess 12, depositing inside it the substance M. This solution may be achieved with a high degree of precision by resorting to a numerical control machine for controlling the relative movement (usually of translation and rotation) of the support 16 that carries the stent 1 and of the dispensing nozzle 25.

The unexpected aspect of this solution, which is apparently very simple, lies in the fact that, contrary to the reasonable expectation of the sector, the pure and simple deposition of the substance M in the form of paste, followed by a treatment of stabilization conducted according to the criteria described previously (and, in a preferred way, by the subsequent contraction of the stent, treated in a radially expanded condition, into a radially contracted condition required, for example, for mounting on the balloon of an insertion catheter), is sufficient to ensure the firm retention of the masses 14 inside the recesses 12. This retention occurs without any risk of dispersion, for example, in the steps of packaging, transportation, manipulation and insertion of the stent in the implantation site.

From the foregoing, it clearly emerges that the individual steps of treatment set forth with reference to the examples seen previously are freely transposable from one context of application to another among the ones previously considered. Furthermore, it is evident that the examples documented above do not exhaust the range of application, nor the variants of embodiment of the solution here described. This applies in particular to the treatments of stabilization which, as has already been mentioned previously, may envisage operations such as: (i) exposure to temperature or to thermal cycles; (ii) dipping in solvent for controlled lengths of time; (iii) exposure to solvent spray, (iv) exposure to solvent vapors; (v) selective treatment with laser beam (exposure of the recesses to laser beams); (vi) selective or integral application of a protective adhesive coating (in the form of a plug for closing the recesses); and (vii) lyophilization.

It will likewise be appreciated that the final result achieved is the location of the active substance M on the surface of the stent 1, in a position directly exposed to the outside, even though usually at least slightly set back in the recesses 12, without the need for providing coatings or sheaths of any sort on the surface of the stent. The surface of the stent thus remains free, with the coating of biocompatible carbon material preferably provided thereon, with consequent beneficial effects both in the implantation site of the stent, and in the steps subsequent to implantation.

Consequently, without prejudice to the principle of the invention, the details of implementation and embodiments may vary with respect to what is described and illustrated herein, without thereby departing from the scope of the present invention.

What is claimed is:

1. A process for depositing an active substance on selected regions of the surface of a stent, comprising:
(i) providing the active substance in at least one form selected from the group consisting of a powder and a paste; and
(ii) depositing the active substance on the selected regions of the surface of the stent,
wherein the stent, with the active substance deposited on the selected regions of the surface of the stent, is subjected to a treatment for stabilizing the active substance to provide adhesion of the active substance to the selected regions, the treatment for stabilizing the active substance being chosen from the group consisting of:
(i) dipping in solvent for a controlled length of time;
(ii) exposure to solvent spray;
(iii) exposure to solvent vapors; and
(iv) lyophilization, and
wherein the stent is not provided with any further coatings or sheath on the surface of the stent, and wherein the solvent is a solvent for the active substance.

2. The process according to claim 1, wherein the process comprises:
(i) coating the active substance on the selected regions and other regions of the surface of the stent; and
(ii) removing the active substance from the other regions of the surface of the stent.

3. The process according to claim 2, wherein the active substance is removed from the other regions of the surface of the stent by jets of fluid.

4. The process according to claim 2, wherein the active substance is removed from the other regions of the surface of the stent by fitting the stent on a nozzle comprising a perforated tube and emitting jets of fluid from the nozzle and through the inside of the stent.

5. The process according to claim 3, wherein the jets of fluid comprise jets of liquid interspersed with puffs of air.

6. The process according to claim 4, wherein the jets of fluid comprise jets of liquid interspersed with puffs of air.

7. The process according to claim 3, wherein the jets of fluid comprise jets of water.

8. The process according to claim 4, wherein the jets of fluid comprise jets of water.

9. The process according to claim 3, wherein the jets of fluid comprise puffs of nitrogen.

10. The process according to claim 4, wherein the jets of fluid comprise puffs of nitrogen.

11. The process according to claim 2, wherein the active substance is removed from the other regions of the surface of the stent by rubbing the surface of the stent with respect to a support.

12. The process according to claim 11, wherein the rubbing support has a compliant surface.

13. The process according to claim 2, wherein the removal of the active substance from the other regions of the surface of the stent is performed before the treatment for stabilizing the active substance.

14. The process according to claim 1, wherein the active substance is applied only on the selected regions of the surface of the stent.

15. The process according to claim 14, wherein the active substance is applied by a dispensing nozzle.

16. The process according to claim 15, wherein a numerical control machine for fine positioning imparts on the dispensing nozzle and/or on the stent a relative movement to apply the active substance.

17. The process according to claim 1, wherein the process comprises:
(i) making a bed or mat of the active substance; and
(ii) exposing the stent to the bed or mat of active substance so that the active substance is transferred at least in part onto the surface of the stent.

18. The process according to claim 17, wherein the stent is exposed to the bed or mat of active substance with application of pressure.

19. The process according to claim 17, wherein the process comprises:
(i) exposing the stent to the bed or mat of active substance in such a way that the active substance coats a surface of the stent, the surface coated comprising the selected regions and the other regions of the surface of the stents; and
(ii) removing the active substance from the other regions of the surface of the stent.

20. The process according to claim 19, wherein the process comprises:
(i) applying on the stent a first mask with first openings, which leave uncovered first selected regions of the stent;
(ii) exposing the stent, with the first mask applied thereto, to the bed or mat of active substance so that the active substance coats the mask and the first selected regions left uncovered by the first openings of the first mask;
(iii) removing the first mask from the stent;
(iv) applying on the stent a second mask with second openings which leave uncovered second selected regions of the stent;
(v) exposing the stent, with the second mask applied thereto, to a bed or mat of a second active substance, so that the second active substance will coat the second mask and the second selected regions left uncovered by the second openings of the second mask; and
(vi) removing the second mask from the stent.

21. The process according to claim 17, wherein the process comprises:
(i) applying on the stent a mask with openings which leave uncovered the selected regions;
(ii) exposing the stent with the mask applied thereto to the bed or mat of active substance, so that the active substance coats the mask and the selected regions left uncovered by the openings of the mask; and
(iii) removing the mask from the stent.

22. The process according to claim 1, wherein the process comprises:
(i) subjecting the stent to an electrostatic charging treatment designed for charging electrostatically at least the selected regions of the surface of the stent; and
(ii) exposing the stent, with at least the selected regions electrostatically charged, to the active substance, the electrostatic charge causing the transfer of the active substance onto the surface of the stent.

23. The process according to claim 22, wherein the process comprises:
(i) subjecting the stent to an electrostatic charging treatment designed for electrostatically charging a surface comprising the selected regions and other regions of the surface of the stent, so that the electrostatic charge causes the transfer of the active substance onto a surface comprising the selected regions and other regions of the surface of the stent; and
(ii) removing the active substance from the other regions of the surface of the stent.

24. The process according to claim 22, wherein the electrostatic charging treatment is by corona effect.

25. The process according to claim 23, wherein the electrostatic charging treatment is by corona effect.

26. The process according to claim 22, wherein before the electrostatic charge treatment, the stent is coated with a layer of biocompatible carbon material.

27. The process according to claim 23, wherein before the electrostatic charge treatment, the stent is coated with a layer of biocompatible carbon material.

28. The process according to claim 1, wherein the process comprises:
(i) providing a transfer support for the active substance;
(ii) subjecting the transfer support to a charging treatment designed for electrostatically charging respective regions of the transfer support homologous with respect to the selected regions of the surface of the stent;
(iii) exposing the transfer support, with the respective electrostatically charged regions, to the active substance, the electrostatic charge determining the transfer of the active substance onto the respective electrostatically charged regions from the transfer support; and
(iv) exposing the transfer support, with the active substance transferred onto the respective electrostatically charged regions, to the surface of the stent, the exposure determining the transfer of the active substance onto the selected regions of the stent.

29. The process according to claim 28, wherein steps (ii), (iii), and (iv) are repeated, employing active substances that each time are different, with the respective electrostatically charged regions of the transfer support being either identical or different for the active substances used.

30. The process according to claim 29, wherein before the electrostatic charge treatment, the stent is coated with a layer of biocompatible carbon material.

31. The process according to claim 28, wherein before the electrostatic charge treatment, the stent is coated with a layer of biocompatible carbon material.

32. The process according to claim 1, wherein the process is performed on the stent when the stent is in a radially contracted condition.

33. The process according to claim 1, wherein the process is performed on the stent when the stent is in a radially expanded condition, and then subjecting the stent to radial contraction.

34. The process according to claim 1, wherein at least some of the selected regions are cavities or recesses in the surface of the stent.

35. The process according to claim 1, wherein the active substance comprises FK506.

36. The process according to claim 35, wherein the active substance consists essentially of FK506 in the form of powder with a grain size not greater than 15 micron.

37. The process according to claim 35, wherein the active substance consists essentially of a paste with a base of FK506 with a viscosity having a value not less than 100,000 to 120,000 cps.

38. The process according to claim 1, wherein the active substance consists essentially of FK506.

39. The process according to claim 1, wherein the treatment for stabilizing the active substance is dipping in solvent for a controlled length of time.

40. The process according to claim 1, wherein the treatment for stabilizing the active substance is exposure to solvent spray.

41. The process according to claim 1, wherein the treatment for stabilizing the active substance is exposure to solvent vapors.

42. The process according to claim 1, wherein the treatment for stabilizing the active substance is lyophilization.

* * * * *